(12) United States Patent
Angot et al.

(10) Patent No.: US 7,678,882 B2
(45) Date of Patent: Mar. 16, 2010

(54) POLYAMINO ACIDS FUNCTIONALIZED BY AT LEAST ONE HYDROPHOBIC GROUP AND THE THERAPEUTIC APPLICATION THEREOF

(75) Inventors: Stéphanie Angot, Lyons (FR); Olivier Breyne, Lyons (FR); You-Ping Chan, Lyons (FR); Gérard Soula, Meyzieu (FR)

(73) Assignee: Flamel Technologies, Vénissieux (FR)

(*) Notice: Subject to any disclaimer, the term of this patent is extended or adjusted under 35 U.S.C. 154(b) by 0 days.

(21) Appl. No.: 11/509,783

(22) Filed: Aug. 25, 2006

(65) Prior Publication Data

US 2007/0160568 A1    Jul. 12, 2007

Related U.S. Application Data

(63) Continuation of application No. 11/311,668, filed on Dec. 20, 2005, now abandoned, which is a continuation of application No. 10/522,556, filed on Jan. 27, 2005, now abandoned.

(51) Int. Cl.
*C07K 2/00* (2006.01)

(52) U.S. Cl. .......................... 530/300; 514/2; 530/329; 530/330; 530/345; 562/571; 562/573

(58) Field of Classification Search ............ 514/2; 530/329, 330, 345, 300; 562/571, 573
See application file for complete search history.

(56) References Cited

U.S. PATENT DOCUMENTS

| | | | |
|---|---|---|---|
| 2,680,749 A | 6/1954 | Cawley et al. |
| 3,536,672 A | 10/1970 | Fujimoto et al |
| 4,126,628 A | 11/1978 | Paquet |
| 4,321,253 A | 3/1982 | Beatty |
| 4,351,337 A | 9/1982 | Sidman |
| 4,443,549 A | 4/1984 | Sadowski |
| 4,450,150 A | 5/1984 | Sidman |
| 4,600,526 A | 7/1986 | Gallot et al. |
| 4,615,697 A | 10/1986 | Robinson |
| 4,652,441 A | 3/1987 | Okada et al. |
| 4,661,345 A | 4/1987 | Tuomanen |
| 4,748,023 A | 5/1988 | Tamas et al. |
| 4,766,106 A | 8/1988 | Katre et al. |
| 4,818,616 A | 4/1989 | Milverton et al. |
| 4,835,293 A | 5/1989 | Bhatia |
| 4,844,905 A | 7/1989 | Ichikawa et al. |
| 4,853,026 A | 8/1989 | Frisch et al. |
| 4,888,398 A | 12/1989 | Bichon et al. |
| 4,892,733 A | 1/1990 | Bichon et al. |
| 4,894,240 A | 1/1990 | Geoghegan et al. |
| 4,904,479 A | 2/1990 | Illum |
| 4,976,968 A | 12/1990 | Steiner |
| 5,023,349 A | 6/1991 | Bhatia |
| 5,084,278 A | 1/1992 | Mehta |
| 5,102,872 A | 4/1992 | Singh et al. |
| 5,204,108 A | 4/1993 | Illum |
| 5,286,495 A | 2/1994 | Batich et al. |
| 5,286,497 A | 2/1994 | Hendrickson et al. |
| 5,399,331 A | 3/1995 | Loughrey et al. |
| 5,449,513 A | 9/1995 | Yokoyama et al. |
| 5,510,103 A | 4/1996 | Yokoyama et al. |
| 5,514,380 A | 5/1996 | Song et al. |
| 5,534,241 A | 7/1996 | Torchilin et al. |
| 5,589,455 A | 12/1996 | Woo |
| 5,609,872 A | 3/1997 | Ahlborg |
| 5,656,722 A | 8/1997 | Dorschug et al. |
| 5,780,579 A | 7/1998 | Soula et al. |
| 5,834,422 A | 11/1998 | Balschmidt et al. |
| 5,852,109 A | 12/1998 | Makino et al. |

(Continued)

FOREIGN PATENT DOCUMENTS

| | | |
|---|---|---|
| CA | 2068366 | 11/1992 |
| EP | 0 198 769 | 10/1986 |
| EP | 0 179 023 | 1/1991 |

(Continued)

OTHER PUBLICATIONS

Hoes, C. J. T. (Journal of Controlled Release 2, 205-13, 1985).*
Akiyoshi et al., *J. Controlled Release* 54: 313-320 (1998).
Microspheres, Microcapsules and Liposomes; vol. 1. Preparation and Chemical Applications, Ed. R. Arshady, Citus Books 1999.
*Sustained-Release Injectable Products*, Ed. J. Senior and M. Radomsky, Interpharm Press 2000, Denver, Colorado.
*Colloidal Drug Delivery Systems*, Ed. J. Kreuter, Marcel Dekker, Inc. 1994.

(Continued)

*Primary Examiner*—David Lukton
(74) *Attorney, Agent, or Firm*—Patton Boggs

(57) ABSTRACT

The invention relates to novel materials based on biodegradable polyamino acids that are useful for vectorizing active principle(s)(AP). The aim of the invention is to supply a new polymeric raw material that is used for vectorizing AP and optimally fulfills all requirements concerning biocompatibility, biodegradability, the ability to be easily associated with numerous active principles or solubilize the active principles and to release the active principles in vivo. Such polymers can also be readily and economically transformed into particles vectorizing active principles according to the grafting rate of the hydrophobic groups, said particles being able to form stable aqueous colloidal suspensions. The aim of the invention is achieved by the inventive amphiphile polyamino acids comprising aspartic and/or glutamic units that carry grafts which encompass at least one hydrophobic unit and are linked to the aspartic and/or glutamic units via a rotula containing two amide functions, more particularly via a spacer of the lysine or ornithine type. The amide functions ensure better stability during hydrolysis than comparable products known in prior art. The invention also relates to new pharmaceutical, cosmetic, dietetic, or phytosanitary compositions based on the inventive polyamino acids.

25 Claims, No Drawings

U.S. PATENT DOCUMENTS

| | | | |
|---|---|---|---|
| 5,863,900 A * | 1/1999 | Russell-Jones | 514/15 |
| 5,869,703 A | 2/1999 | Kim et al. | |
| 5,872,210 A | 2/1999 | Medabalimi | |
| 5,876,969 A | 3/1999 | Fleer et al. | |
| 5,904,936 A | 5/1999 | Huille et al. | |
| 5,981,761 A * | 11/1999 | Chou et al. | 548/339.1 |
| 6,143,314 A | 11/2000 | Chandrashekar et al. | |
| 6,153,193 A | 11/2000 | Kabanov et al. | |
| 6,180,141 B1 | 1/2001 | Lemercier et al. | |
| 6,193,953 B1 | 2/2001 | Lohrmann et al. | |
| 6,197,535 B1 | 3/2001 | Bandyopadhyay et al. | |
| 6,201,072 B1 | 3/2001 | Rathi et al. | |
| 6,235,282 B1 | 5/2001 | Riviere et al. | |
| 6,284,267 B1 | 9/2001 | Aneja | |
| 6,309,633 B1 | 10/2001 | Ekwuribe et al. | |
| 6,313,095 B1 | 11/2001 | Adams et al. | |
| 6,313,260 B2 * | 11/2001 | Gruning et al. | 528/310 |
| 6,320,017 B1 | 11/2001 | Ansell | |
| 6,500,448 B1 | 12/2002 | Johnson et al. | |
| 6,576,254 B1 | 6/2003 | Uchegbu | |
| 6,630,171 B1 | 10/2003 | Huille et al. | |
| 6,933,269 B2 * | 8/2005 | Jordan et al. | 510/480 |
| 6,946,146 B2 | 9/2005 | Mulye | |
| 7,030,155 B2 | 4/2006 | Lambert et al. | |
| 7,226,618 B1 | 6/2007 | Touraud et al. | |
| 7,261,875 B2 * | 8/2007 | Li et al. | 424/1.69 |
| 7,270,832 B2 | 9/2007 | Bryson et al. | |
| 2001/0000510 A1 | 4/2001 | Sakurai et al. | |
| 2002/0068085 A1 | 6/2002 | Rudnic et al. | |
| 2003/0133980 A1 | 7/2003 | Costantino et al. | |
| 2004/0038885 A1 | 2/2004 | Bryson et al. | |
| 2004/0063628 A1* | 4/2004 | Piccariello et al. | 514/12 |
| 2004/0071716 A1 | 4/2004 | Jansen et al. | |
| 2004/0175424 A1 | 9/2004 | Castan et al. | |
| 2005/0158392 A1 | 7/2005 | Kim et al. | |
| 2006/0099264 A1 | 5/2006 | Chan et al. | |
| 2007/0010652 A1 | 1/2007 | Angot et al. | |
| 2007/0160568 A1 | 7/2007 | Angot et al. | |
| 2007/0178126 A1 | 8/2007 | Angot et al. | |
| 2007/0190162 A1 | 8/2007 | Caillol et al. | |
| 2007/0196497 A1 | 8/2007 | Pouliquen et al. | |
| 2007/0248686 A1 | 10/2007 | Touraud et al. | |
| 2007/0254828 A1 | 11/2007 | Dubreucq et al. | |
| 2007/0265192 A1 | 11/2007 | Soula et al. | |
| 2008/0014250 A1 | 1/2008 | Soula et al. | |
| 2008/0015332 A1 | 1/2008 | Bryson et al. | |
| 2009/0012028 A1 | 1/2009 | Chan et al. | |
| 2009/0110742 A1 | 4/2009 | Constancis et al. | |

FOREIGN PATENT DOCUMENTS

| | | |
|---|---|---|
| EP | 0 583 955 | 2/1994 |
| EP | 0 601 508 | 6/1994 |
| EP | 0 721 776 | 7/1996 |
| EP | 0 734 720 | 10/1996 |
| EP | 0 963 758 | 12/1999 |
| FR | 2 533 209 | 3/1984 |
| FR | 2 732 218 | 10/1996 |
| FR | 2 746 035 | 9/1997 |
| FR | 2 786 098 | 5/2000 |
| FR | 2 838 964 | 10/2003 |
| FR | 2 840 614 | 12/2003 |
| FR | 2 843 117 | 2/2004 |
| FR | 2 855 521 | 12/2004 |
| FR | 2 860 516 | 4/2005 |
| FR | 2 873 040 | 1/2006 |
| FR | 2 915 748 | 11/2008 |
| GB | 966 760 | 8/1964 |
| GB | 1 024 393 | 3/1966 |
| GB | 1 202 765 | 8/1970 |
| GB | 2 041 517 | 9/1980 |
| GB | 2 240 547 | 8/1991 |
| WO | WO 85/002092 | 5/1985 |
| WO | WO 87/002219 | 4/1987 |
| WO | WO 87/003891 | 7/1987 |
| WO | WO 88/001213 | 2/1988 |
| WO | WO 88/007078 | 9/1988 |
| WO | WO 89/008449 | 9/1989 |
| WO | WO 91/006286 | 5/1991 |
| WO | WO 91/006287 | 5/1991 |
| WO | WO 96/029991 | 10/1996 |
| WO | WO 96/040279 | 12/1996 |
| WO | WO 97/002810 | 1/1997 |
| WO | WO 97/034584 | 9/1997 |
| WO | WO 98/011874 | 3/1998 |
| WO | WO 99/018142 | 4/1999 |
| WO | WO 99/061512 | 12/1999 |
| WO | WO-9961512 | 12/1999 |
| WO | WO 00/018821 | 4/2000 |
| WO | WO 00/030618 | 6/2000 |
| WO | WO 00/071163 | 11/2000 |
| WO | WO 00/78791 | 12/2000 |
| WO | WO 01/037809 | 5/2001 |
| WO | WO 02/028521 | 4/2002 |
| WO | WO 02/039984 | 5/2002 |
| WO | WO 02/098951 | 12/2002 |
| WO | WO 02/098952 | 12/2002 |
| WO | WO 03/002096 | 1/2003 |
| WO | WO 03/013467 | 2/2003 |
| WO | WO 03/104303 | 12/2003 |
| WO | WO 04/013206 | 2/2004 |
| WO | WO 04/060968 | 7/2004 |
| WO | WO 04/108796 | 12/2004 |
| WO | WO 05/033181 | 4/2005 |
| WO | WO 05/051416 | 6/2005 |
| WO | WO 06/016078 | 2/2006 |
| WO | WO 07/034320 | 3/2007 |
| WO | WO 07/116143 | 10/2007 |

OTHER PUBLICATIONS

*Handbook of Pharmaceutical Controlled Release Technology*, Ed. D.L. Wise, Marcel Dekker, Inc. 2000, New York, New York.

Fuller et al., *A Procedure for the Facile Synthesis of Amino-Acid N-Carboxyanhydries*, Biopolymers 15: 1869 (1976).

Tomida et al., "Convenient Synthesis Of High Molecular Weight Poly(Succinimide) By Acid-Catalysed Polycondensation of L-Aspartic Acid," Polymer, 1997, vol. 38, No. 18, pp. 4733-4736.

In the U.S. Patent and Trademark Office, Non-Final Office Action in re: U.S. Appl. No. 08/592,299, dated May. 5, 1997, 3 pages.

In the U.S. Patent and Trademark Office, Non-Final Office Action in re: U.S. Appl. No. 08/592,299, dated Oct. 4, 1996, 6 pages.

In the U.S. Patent and Trademark Office, Final Office Action in re: U.S. Appl. No. 08/621,438, dated Apr. 22, 1998, 1 page.

In the U.S. Patent and Trademark Office, Non-Final Office Action in re: U.S. Appl. No. 08/621,438, dated Feb. 13, 1997, 4 pages.

In the U.S. Patent and Trademark Office, Non-Final Office Action in re: U.S. Appl. No. 08/621,438, dated Jul. 24, 1997, 5 pages.

In the U.S. Patent and Trademark Office, Non-Final Office Action in re: U.S. Appl. No. 09/147,032, dated Jul. 6, 1999, 5 pages.

In the U.S. Patent and Trademark Office, Final Office Action in re: U.S. Appl. No. 09/856,378, dated Jan. 28, 2003, 11 pages.

In the U.S. Patent and Trademark Office, Final Office Action in re: U.S. Appl. No. 09/856,378, dated Sep. 27, 2002, 7 pages.

In the U.S. Patent and Trademark Office, Final Office Action in re: U.S. Appl. No. 10/130,783, dated Jan. 27, 2006, 19 pages.

In the U.S. Patent and Trademark Office, Final Office Action in re: U.S. Appl. No. 10/398,133, dated Mar. 24, 2009, 8 pages.

In the U.S. Patent and Trademark Office, Non-Final Office Action in re: U.S. Appl. No. 10/398,133, dated Jun. 13, 2008, 13 pages.

In the U.S. Patent and Trademark Office, Non-Final Office Action in re: U.S. Appl. No. 10/398,133, dated Nov. 4, 2005, 10 pages.

In the U.S. Patent and Trademark Office, Non-Final Office Action in re: U.S. Appl. No. 10/398,133, dated Sep. 28, 2007, 15 pages.

In the U.S. Patent and Trademark Office, Non-Final Office Action in re: U.S. Appl. No. 10/398,134, dated Oct. 17, 2006, 14 pages.
In the U.S. Patent and Trademark Office, Non-Final Office Action in re: U.S. Appl. No. 10/398,134, dated May. 12, 2005, 11 pages.
In the U.S. Patent and Trademark Office, Final Office Action in re: U.S. Appl. No. 10/473,821, dated Dec. 31, 2008, 5 pages.
In the U.S. Patent and Trademark Office, Final Office Action in re: U.S. Appl. No. 10/473,821, dated Jan. 19, 2007, 10 pages.
In the U.S. Patent and Trademark Office, Non-Final Office Action in re: U.S. Appl. No. 10/473,821, dated Aug. 29, 2005, 12 pages.
In the U.S. Patent and Trademark Office, Non-Final Office Action in re: U.S. Appl. No. 10/473,821, dated Mar. 24, 2008, 9 pages.
In the U.S. Patent and Trademark Office, Non-Final Office Action in re: U.S. Appl. No. 10/473,821, dated May. 2, 2006, 8 pages.
In the U.S. Patent and Trademark Office, Final Office Action in re: U.S. Appl. No. 10/516,733, dated Jun. 17, 2008, 9 pages.
In the U.S. Patent and Trademark Office, Non-Final Office Action in re: U.S. Appl. No. 10/516,733, dated Feb. 26, 2009, 4 pages.
In the U.S. Patent and Trademark Office, Non-Final Office Action in re: U.S. Appl. No. 10/516,733, dated Feb. 5, 2007, 7 pages.
In the U.S. Patent and Trademark Office, Non-Final Office Action in re: U.S. Appl. No. 10/516,733, dated Sept. 12, 2007, 7 pages.
In the U.S. Patent and Trademark Office, Final Office Action in re: U.S. Appl. No. 10/558,617, dated Jun. 26, 2009, 14 pages.
In the U.S. Patent and Trademark Office, Final Office Action in re: U.S. Appl. No. 10/558,617, dated Jan. 30, 2008, 8 pages.
In the U.S. Patent and Trademark Office, Non-Final Office Action in re: U.S. Appl. No. 10/558,617, dated Dec. 22, 2008, 8 pages.
In the U.S. Patent and Trademark Office, Non-Final Office Action in re: U.S. Appl. No. 10/558,617, dated Jun. 29, 2007, 10 pages.
In the U.S. Patent and Trademark Office, Non-Final Office Action in re: U.S. Appl. No. 10/580,035, dated Dec. 3, 2008, 25 pages.
In the U.S. Patent and Trademark Office, Non-Final Office Action in re: U.S. Appl. No. 11/601,691, dated Apr. 3, 2009, 29 pages.
In the U.S. Patent and Trademark Office, Non-Final Office Action in re: U.S. Appl. No. 11/878,947, dated Jul. 20, 2009, 11 pages.
In the U.S. Patent and Trademark Office, Final Office Action in re: U.S. Appl. No. 10/574,475, dated Nov. 07, 2008, 4 pages.
In the U.S. Patent and Trademark Office, Final Office Action in re: U.S. Appl. No. 10/574,475, dated Jan. 31, 2008, 8 pages.
Akiyoshi et al., "Stabilization of Insulin upon Supramolecular Complexation with Hydrophobized Polysaccharide Nanoparticle," *Chemistry Letters*, 1995; 8:707-708.
Candau, S., Chapter 3: Light Scattering *Surfactant Solutions*, 1984; 22:147-207.
Davis, J.T., "A Quantitative Kinetic Theonj of Emulsion Type, I. Physical Chemistry of the Emulsifying Agent," *Proceedings of the Second International Congress of Surface Activity*, 1957; pp. 426-439.
Forssen et al., "Improved Therapeutic Benefits of Doxorubicin by Entrapment in Anionic Liposomes," *Cancer Res.*, 1983; 43:546-550.
Gao et al., "Measurement of the Binding of Proteins to Polyelectrolytes by Frontal Analysis Continuous Capillary Electrophoresis," *Anal. Chem.*, 1997; 69:2945-2951.

Griffin, G.C., "Classification of Surface-Active Agents by 'HLB'," *Journal of the Society of Cosmetic Chemists*, 1949; 1(5):311-327.
"Viscosities of Liquids" *Handbook of Chemistry and Physics*, 88th Ed., 2008; 6:175-179.
Harada et al., "Formation of Polyion Complex Micelles in an Aqueous Milieu from a Pair of Oppositely-Charged Block Copolymers with Poly(ethylene glycol) Segments," *Macromolecules*, 1995; 28:5294-5299.
Hudecz et al., "Branched Polypeptides with a POLY-(L-Lysine) Backbone: Synthesis, Conformation, and Immunomodulation," *Polymeric Materials in Medication*, Plenum Press, New York, 1985; pp. 265-89.
Illum et al., "Effect of the Nonionic Surfactant Poloxamer 338 on the Fate and Deposition of Polystyrene Microspheres Following Intravenous Administration," *J. Pharm. Sci.*, 1983; 72(9):1086-1089.
Jaworek et al., "Effects of Analogs of (pyro)Glu-His-Gly-OH on Food Consumption and Gastric Acid Secretion in Rats," *Life Science*, 1984; 34(26):2597-2603.
English Abstract for Kataoka, K. "Preparation of Novel Drug Carrier based on the Self-Association of Block Copolymer," *Drug Delivery System*, 1995; 10 5:363-370.
Kuroda et al., "Hierarchical Self-Assembly of Hydrophobically Modified Pullulan in Water Gelation by Networks of Nanoparticles," *Langmuir*, 2002; 18:3780-3786.
Maa et al., "Spray-Drying of Air-Liquid Interface Sensitive Recombinant Human Growth Hormone," *Journal of Pharmaceutical Sciences*, 1988; 87(2):152-159.
Mezo et al., "Synthesis and Conformation Studies of Poly(L-Lysine) Based Polypeptides with 1 Ser and Glu/Leu in the Side Chains," J. Controlled Release, 2000; 63:81-95.
Oppenheim et al., "The Primary Structure and Functional Characterization of the Neutral Histidine-Rich Polypeptide from Human Parotid Secretion," *Journal of Biological Chemistry*, 1986; 261(3):1177-1182.
Regalado et al., "Viscoelastic Behavior of Semidilute Solutions of Multisticker Polymer Chains," *Macromolecules*, 1999; 32:8580-8588.
Shen, W.C., "Acid Sensitive Dissociative Between Poly (Lysine) and Histamine Modified Poly (Glutamate) as a Model for Drug Releasing From Carriers in Endosomes," 1990, *Biochim. Biophys. Acts.*, 1034(1):122-124.
Tsutsumiuchi et al., "Synthesis of Polyoxazoline-(Glyco)peptide Block Copolymer Ring-opening Polymerization of (Sugar-Substituted) a Amino Acid N-Carboxyanhydrides with Polyoxazoline Macroinitiators," *Macromolecules*, 1997; 30:4013-4017.
Van Heeswijk et al., "The Synthesis and Characterization of Polypeptide-Adriamycin Conjugates and its Complexes with Adriamycin," *J. Controlled Release*, 1985; 1(4):301-315.
English Summary for Volgler et al., *Holv. Chim. Acta*, 1964; 47:526-544.
Woodle et al., "Sterically Stabilized Liposomes," *Biochim. Biophys. Acta*, 1992; 1113(2):171-199.
Woodle, M.C., "Controlling Liposome Blood Clearance by Surface-Grafted Polymers," *Adv. Drug Deliv. Rev.*, 1998; 32(1-2):139-152.

\* cited by examiner

POLYAMINO ACIDS FUNCTIONALIZED BY AT LEAST ONE HYDROPHOBIC GROUP AND THE THERAPEUTIC APPLICATION THEREOF

This application is a Continuation of application Ser. No. 11/311,668, filed Dec. 20, 2005, now abandoned, which is a Continuation of application Ser. No. 10/522,556, filed Jan. 27, 2005, now abandoned, which is a National Stage of Application No. PCT/FR2003/002329, filed Jul. 23, 2003. and claims priority to French Application No. 02 0 9670, filed Jul. 20, 2002.

The present invention relates to novel materials based on biodegradable polyamino acids that are useful especially for the vectorization of active principle(s) (AP).

The invention further relates to novel pharmaceutical, cosmetic, dietetic or phytosanitary compositions based on these polyamino acids. These compositions can be of the types that allow the vectorization of AP and preferably take the form of emulsions, micelles, particles, gels, implants or films.

The AP considered are advantageously biologically active compounds capable of being administered to an animal or human organism by the oral, parenteral, nasal, vaginal, ocular, subcutaneous, intravenous, intramuscular, intradermal, intraperitoneal, intracerebral or buccal route, etc.

The AP to which the invention relates more particularly, but without implying a limitation, are proteins, glycoproteins, peptides, polysaccharides, lipopolysaccharides, oligonucleotides or polynucleotides, and organic molecules. However, the invention can also relate to cosmetic products or to phytosanitary products such as herbicides, insecticides, fungicides, etc.

In the field of the vectorization of active principles, especially medicinal active principles, there is a need in many cases to:
- protect them from degradation (hydrolysis, precipitation at the site, enzymatic digestion, etc.) until they reach their site of action,
- and/or control their release rate so as to maintain a constant level over a defined period, or
- and/or convey them (with protection) to the site of action.

Several types of polymers have been studied for these purposes and some are even available commercially. Examples which may be mentioned are polymers of the polylactic, polylactic-glycolic, polyoxyethylene-oxypropylene, polyamino acid or polysaccharide type. These polymers constitute starting materials for the manufacture e.g. of mass implants, microparticles, nanoparticles, vesicles, micelles or gels. Apart from the fact that these polymers have to be suitable for the manufacture of such systems, they also have to be biocompatible, non-toxic, non-immunogenic and economic and they must be easily removable from the body and/or biodegradable. On this last point, it is additionally essential that biodegradation in the organism generates non-toxic products.

Various patents, patent applications or scientific articles are referred to below in order to illustrate the prior art concerning polymers employed as starting materials for the production of AP vectorization systems.

U.S. Pat. No. 4,652,441 describes polylactide microcapsules encapsulating the hormone LH-RH. These microcapsules are produced by preparing a water-in-oil-in-water emulsion and comprise an aqueous inner layer containing the hormone, a substance (gelatin) for fixing the latter, an oily layer of polylactide and an aqueous outer layer (polyvinyl alcohol). The AP can be released over a period of more than two weeks after subcutaneous injection.

U.S. Pat. No. 6,153,193 describes compositions based on amphiphilic polyoxyethylene-polyoxypropylene micelles for the vectorization of anticancer agents such as adriamycin.

Akiyoshi et al. (J. Controlled Release 1998, 54, 313-320) describe pullulans which are rendered hydrophobic by the grafting of cholesterol and which form nanoparticles in water. These nanoparticles, which are capable of complexing reversibly with insulin, form stable colloidal suspensions.

U.S. Pat. No. 4,351,337 describes amphiphilic copolyamino acids based on leucine and glutamate which can be used in the form of implants or microparticles for the controlled release of active principles. The latter can be released over a very long period that depends on the degradation rate of the polymer.

U.S. Pat. No. 4,888,398 describes polymers based on polyglutamate or polyaspartate, and optionally polyleucine, with pendent groups of the alkoxycarbonylmethyl type located randomly along the polyamino acid chain. These polyamino acids, grafted with side groups, e.g. methoxycarbonylmethyl groups, can be used in the form of biodegradable implants containing a prolonged-release AP.

U.S. Pat. No. 5,904,936 describes nanoparticles obtained from a polyleucine-polyglutamate block polymer which are capable of forming stable colloidal suspensions and of associating spontaneously with biologically active proteins without denaturing them. The latter can then be released in vivo in a controlled manner over a long period.

U.S. Pat. No. 5,449,513 describes amphiphilic block copolymers comprising a polyoxyethylene block and a polyamino acid block, for example poly(beta-benzyl-L-aspartate). These polyoxyethylene-polybenzylaspartate polymers form micelles that are capable of encapsulating hydrophobic active molecules such as adriamycin or indomethacin.

Patent application WO 99/61512 describes polylysines and polyornithines functionalized by a hydrophobic group (palmitic acid bonded to polylysine or ornithine) and a hydrophilic group (polyoxyethylene). In the presence of cholesterol, these polymers, for example polylysine grafted with polyoxyethylene and palmitoyl chains, form vesicles capable of encapsulating doxorubicin or DNA. These polymers based on polylysines are cationic in a physiological medium.

Patent application WO 00/30618, in the name of the Applicant, describes poly(sodium glutamate)(methyl, ethyl, hexadecyl or dodecyl polyglutamate) block or random polymers capable of forming stable colloidal suspensions and of associating spontaneously with biologically active proteins without denaturing them. The latter can be released in vivo in a controlled manner over a long period. These amphiphilic copolyamino acids are modified by the presence of a hydrophobic alkyl side chain. These alkyl groups are covalently grafted onto the polymer via an ester group resulting from the reaction of an alcohol or an iodoalkane (precursor of the alcohol graft) with the carboxyl group of the glutamic unit. These polymers are anionic in a physiological medium.

They are capable of improvement in at least two respects, depending on the intended application:
- the relative stability of the ester group in an aqueous medium,
- and the use of certain non-natural alcohols, such as hexanol, as precursors of hydrophobic alkyl grafts. The latter aspect is particularly problematic in terms of toxicity if the amount of polymer containing residues of such alcohols becomes large.

Thus, even though a very large number of technical solutions exist in the prior art that have been developed and proposed for the vectorization of medicinal active principles, the answer to the demands as a whole is difficult to achieve and remains unsatisfactory.

In this context, one of the essential objects of the present invention is to provide a novel subfamily of polymers (preferably anionic polymers) based on polyglutamate and polyaspartate which represent an improvement compared with the polymers described in patent application WO-A-00/30618.

According to another essential object of the present invention, these improved polymers should be capable of being used for the vectorization of AP and should make it possible optimally to satisfy all the following specifications of the specifications sheet:
biocompatibility,
biodegradability,
stability to hydrolysis,
these polymers themselves being capable of:
easily and economically forming stable aqueous colloidal suspensions,
easily associating with numerous active principles,
and releasing these active principles in vivo.

This and other objects are achieved by the present invention, which relates first and foremost to an amphiphilic polyamino acid comprising aspartic units and/or glutamic units carrying grafts, each of which contains at least one hydrophobic unit, characterized in that at least some of these hydrophobic grafts are bonded to the aspartic and/or glutamic units, each by way of a "spacer" forming part of and/or comprising at least two amide linkages.

According to the invention, a hydrophobic unit derived from an acid or from one of its derivatives, preferably a natural fatty acid, is selected and this hydrophobic acid is then grafted onto the polymer via a "spacer" preferably based on lysine or ornithine. The two linkages involved in the grafting of the hydrophobic group are amides (of the same type as the peptide linkages of the polyamino acid). The inventive concept is therefore based partly on the use of hydrophobic acids as precursors of the grafts, instead of the known alcohols or iodoalkyls, affording polymers that are much more stable in an aqueous medium.

These novel polymers have a biodegradable skeleton based on a polyamino acid carrying side chains which comprise a hydrophobic unit. These polymers have surprising association and/or encapsulation properties compared with analogous products; furthermore, they are readily degraded in the presence of enzymes.

It is to the Applicant's credit to have had the idea of combining, in a totally judicious and advantageous manner, particular biodegradable and anionic polyAsp and/or polyGlu polyamino acids with grafts that contain at least one hydrophobic unit derived from an acid and are bonded to the polyAsp and/or polyGlu skeleton via a rotating linkage comprising at least two amide groups, and more precisely via a "spacer" based on lysine (or, more preferably, L-lysine) or ornithine.

These novel (co)polymers have proved particularly suitable for the vectorization of AP.

In terms of the invention, the words "polyamino acid" cover both oligoamino acids comprising from 2 to 20 amino acid units and polyamino acids comprising more than 20 amino acid units.

Preferably, the polyamino acids according to the present invention are oligomers or homopolymers comprising glutamic or aspartic amino acid repeat units or copolymers comprising a mixture of these two types of amino acid units. The units in question in these polymers are amino acids having the D, L or D,L configuration and are bonded via their alpha or gamma positions in the case of the glutamate or glutamic unit and via their alpha or beta positions in the case of the aspartic or aspartate unit.

The preferred amino acid units are those having the L configuration and a linkage of the alpha type.

Even more preferably, the polyamino acids according to the invention have general formula (I) below:

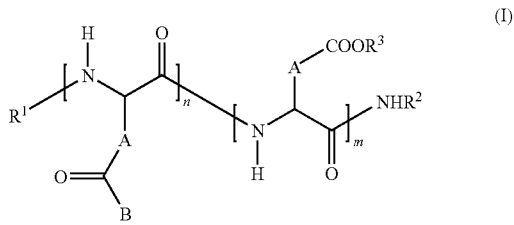

in which:
R$^1$ is H, a linear C2 to C10 acyl group or branched C3 to C10 acyl group, or a pyroglutamate;
R$^2$ is H, a linear C2 to C10 alkyl or branched C3 to C10 alkyl, benzyl or a terminal amino acid unit;
R$^3$ is H or a cationic entity preferably selected from the group comprising:
metal cations advantageously selected from the subgroup comprising sodium, potassium, calcium and magnesium,
organic cations advantageously selected from the subgroup comprising:
cations based on amine,
cations based on oligoamine,
cations based on polyamine (polyethylenimine being particularly preferred),
and cations based on amino acid(s) advantageously selected from the class comprising cations based on lysine or arginine,
and cationic polyamino acids advantageously selected from the subgroup comprising polylysine and oligolysine;
the n groups B independently of one another are each a monovalent radical of the following formula:

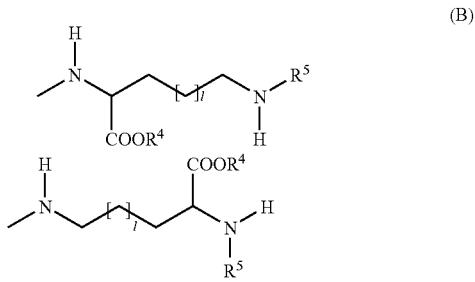

in which:
R$^4$ independently is a group selected from the list given for R$^3$, a linear C1 to C6 alkyl, a branched C3 to C8 alkyl or a benzyl;
and R$^5$ independently is a group selected from acid derivatives such as those derived from (i) saturated or unsaturated, linear C2 to C24 or branched C4 to C24 alkyls, or (ii) C7 to C24 aryls, aralkyls or alkylaryls;

A independently is —CH$_2$— (aspartic unit) or —CH$_2$—CH$_2$— (glutamic unit);

n/(n+m) is defined as the molar grafting rate and varies from 0.5 to 100 mol %;

n+m varies from 3 to 1000 and preferably between 30 and 300;

and 1 is equal to 1 (ornithine "spacer") or 2 (lysine "spacer").

In general the preferred radicals —R$^5$ are acyls derived from natural fatty acids preferably selected from the group comprising palmitic acid, stearic acid, oleic acid and linoleic acid.

In a first embodiment of the invention, the polyamino acids are alpha-L-glutamate or alpha-L-glutamic homopolymers.

In a second embodiment of the invention, the polyamino acids are alpha-L-aspartate or alpha-L-aspartic homopolymers.

In a third embodiment of the invention, the polyamino acids are alpha-L-aspartate/alpha-L-glutamate or alpha-L-aspartic/alpha-L-glutamic copolymers.

Advantageously, the distribution of the aspartic and/or glutamic units carrying grafts containing at least one hydrophobic unit is such that the resulting polymers are either random or of the block type or of the multiblock type.

Defined in another way, the polyamino acids according to the invention have a molecular weight of between 2000 and 100,000 g/mol and preferably of between 5000 and 40,000 g/mol.

As a further preference, the molar grafting rate of hydrophobic units in the polyamino acids according to the invention should be between 2 and 50% and preferably between 5 and 20%.

Remarkably, the polyamino acids of the invention can be used in several ways according to the grafting rate. The methods of shaping a polymer for the encapsulation of an active principle in the various forms to which the invention relates are known to those skilled in the art. Further details can be obtained e.g. by consulting the few particularly pertinent references given below:

"*Microspheres, Microcapsules and Liposomes*; vol. 1. *Preparation and chemical applications*", Ed. R. Arshady, Citus Books 1999. ISBN: 0-9532187-1-6.

"*Sustained-Release Injectable Products*", Ed. J. Senior and M. Radomsky, Interpharm Press 2000. ISBN: 1-57491-101-5.

"*Colloidal Drug Delivery Systems*", Ed. J. Kreuter, Marcel Dekker, Inc. 1994. ISBN: 0-8247-9214-9.

"*Handbook of Pharmaceutical Controlled Release Technology*", Ed. D. L. Wise, Marcel Dekker, Inc. 2000. ISBN: 0-8247-0369-3.

Polyamino acids are also extremely valuable in that, with a relatively low grafting rate in the order of 3 to 10%, they disperse in water at pH 7.4 (e.g. with a phosphate buffer) to give colloidal solutions or suspensions, or gels according to the polymer concentration and the grafting rate. Furthermore, polyamino acids (in particulate or non-particulate form) can encapsulate or associate easily with active principles such as proteins, peptides or small molecules. The preferred shaping operation is that described in patent application WO 00/30618 in the name of the Applicant, which consists in dispersing the polymer in water and incubating the solution in the presence of an AP. This solution can subsequently be filtered on a 0.2 μm filter and then injected directly into a patient.

Beyond a grafting rate of 10%, the polymer can form microparticles capable of associating or encapsulating AP. In this context the microparticles can be shaped by cosolubilizing the AP and the polymer in an appropriate organic solvent and then precipitating the mixture in water. The particles are subsequently recovered by filtration and can then be used for administration by the oral route (in the form of gelatin capsules, in a compacted and/or coated form, or else in a form dispersed in an oil) or by the parenteral route, after redispersion in water.

At grafting rates in excess of 30%, redispersion of the polymer in an aqueous phase becomes more difficult because of the smaller amount of ionizable carboxylate groups, and the polymer precipitates. In this case the polymer can be solubilized in a biocompatible solvent, such as N-methylpyrrolidone, or an appropriate oil, such as Mygliol®, and then injected by the intramuscular or subcutaneous route or into a tumor. Diffusion of the solvent or oil leads to precipitation of the polymer at the injection site and thus forms a deposit. These deposits then assure a controlled release of the polymer by diffusion and/or by erosion and/or by hydrolytic or enzymatic degradation.

In general the polymers of the invention, in neutral or ionized form, can be used by themselves or in a liquid, solid or gel composition and in an aqueous or organic medium.

It should be understood that the polymer based on polyamino acids contains carboxyl groups which are either neutral (COOH form) or ionized, depending on the pH and the composition. For this reason the solubility in an aqueous phase is a direct function of the proportion of free COOH in the polymer (not grafted with the hydrophobic unit) and those in the "spacer" (COOR$^4$ where R$^4$ is H) and of the pH. In aqueous solution the countercation can be a metal cation such as sodium, calcium or magnesium, or an organic cation such as triethanolamine, tris(hydroxymethyl)aminomethane or a polyamine like polyethylenimine.

The polymers of the invention are obtained by methods known to those skilled in the art. The polyamino acids can be obtained by grafting with the lysine or ornithine "spacer" which has been functionalized beforehand on one of the amino ends by a hydrophobic group.

For example, a homopolyglutamate or homopolyaspartate polyamino acid or a block, multiblock or random glutamate/aspartate copolymer is prepared by conventional methods.

To obtain a polyamino acid of the alpha type, the most common technique is based on the polymerization of amino acid N-carboxy anhydrides (NCA), which is described e.g. in the article "*Biopolymers*" 1976, 15, 1869, and in the work by H. R. Kricheldorf entitled "*Alpha-amino acid N-carboxy anhydride and related heterocycles*", Springer Verlag (1987). The NCA derivatives are preferably NCA—O—Me, NCA—O—Et or NCA—O—Bz derivatives (Me=methyl, Et=ethyl and Bz=benzyl). The polymers are then hydrolyzed under appropriate conditions to give the polymer in its acid form. These methods are based on the description given in patent FR-A-2 801 226 in the name of the Applicant. A number of polymers that can be used according to the invention, for example of the poly(alpha-L-aspartic), poly(alpha-L-glutamic), poly(alpha-D-glutamic) and poly(gamma-L-glutamic) types of variable molecular weights, are commercially available. The polyaspartic polymer of the alpha-beta type is obtained by the condensation of aspartic acid (to give a polysuccinimide) followed by basic hydrolysis (cf. Tomida et al., Polymer 1997, 38, 4733-36).

The hydrophobic graft with an amine group can be prepared by one of the methods proposed below. By way of example, the lysine-type "spacer" is the one chosen to illustrate the method of preparation.

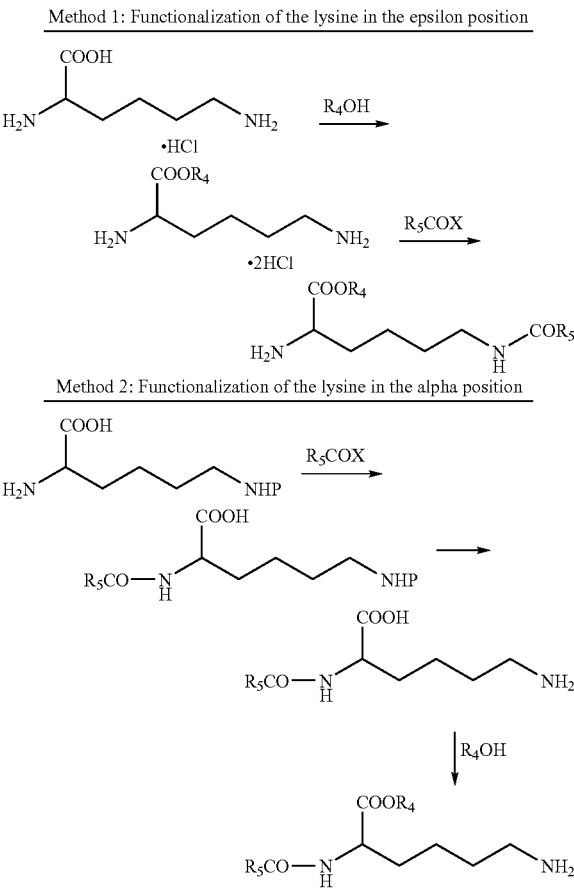

In these schemes X is a leaving group such as a halide or an N-hydroxysuccinimide and P is an amine-protecting group such as N-benzyloxycarbonyl (Cb) or t-Boc. The following two references may be cited for a general or complementary description of the method: U.S. Pat. No. 4,126,628 and Volgler et al., *Helv. Chim. Acta* 1964, 47, 526-544.

Coupling of the resulting amine with an acid group of the polymer is easily effected by reacting the polyamino acid in the presence of a carbodiimide as coupling agent, and optionally a catalyst such as 4-dimethylaminopyridine, in an appropriate solvent such as dimethylformamide (DMF), N-methylpyrrolidone (NMP) or dimethyl sulfoxide (DMSO). The carbodiimide is e.g. dicyclohexylcarbodiimide or diisopropylcarbodiimide. The grafting rate is controlled chemically by the stoichiometry of the constituents and reactants or by the reaction time.

According to another of its features, the invention relates to a pharmaceutical, cosmetic, dietetic or phytosanitary composition comprising at least one polyamino acid as defined above and optionally at least one active principle, which can be a therapeutic, cosmetic, dietetic or phytosanitary active principle.

Preferably, the active principle is a protein, a glycoprotein, a protein bonded to one or more polyalkylene glycol chains {preferably polyethylene glycol (PEG) chains: "PEGylated protein"}, a polysaccharide, a liposaccharide, an oligonucleotide, a polynucleotide or a peptide.

Even more preferably, the active principle is a small hydrophobic, hydrophilic or amphiphilic organic molecule.

This composition can be in the form of nanoparticles, microparticles, emulsions, gels, micelles, implants, powders or films.

In one of its particularly preferred forms, the composition, whether or not laden with active principle(s), is a stable colloidal suspension of nanoparticles and/or microparticles and/or micelles of polyamino acids in an aqueous phase.

If the composition according to the invention is a pharmaceutical composition, it can be administered by the oral, parenteral, nasal, vaginal, ocular, subcutaneous, intravenous, intramuscular, intradermal, intraperitoneal, intracerebral or buccal route.

It is also possible to envisage a composition in the form of a solution in a biocompatible solvent that can be injected by the subcutaneous or intramuscular route or into a tumor.

In another variant, the composition according to the invention is formulated in such a way that it is capable of forming a deposit at the injection site.

The invention further relates to compositions which comprise polyamino acids according to the invention and AP and which can be used for the preparation of:

drugs, particularly for administration by the oral, nasal, vaginal, ocular, subcutaneous, intravenous, intramuscular, intradermal, intraperitoneal or intracerebral route, it being possible in particular for the active principles of these drugs to be proteins, glycoproteins, proteins bonded to one or more polyalkylene glycol chains {e.g. polyethylene glycol (PEG) chains, in which case the term "PEGylated" proteins is used}, peptides, polysaccharides, liposaccharides, oligonucleotides, polynucleotides and small hydrophobic, hydrophilic or amphiphilic organic molecules;

and/or nutriments;

and/or cosmetic or phytosanitary products.

This preparation is characterized in that it consists essentially in using at least one of the polyamino acids according to the invention, as defined above, and/or the composition also described above.

As indicated above, the techniques of associating one or more AP with the grafted polyamino acids according to the invention are described especially in patent application WO-A-00/30618.

The invention further relates to a method of therapeutic treatment that consists essentially in administering the composition as described in the present disclosure by the oral, parenteral, nasal, vaginal, ocular, subcutaneous, intravenous, intramuscular, intradermal, intraperitoneal, intracerebral or buccal route.

The invention further relates to a method of therapeutic treatment that consists essentially in providing a composition as described above, in the form of a solution in a biocompatible solvent, and then injecting it by the subcutaneous or intramuscular route or into a tumor, preferably in such a way that it forms a deposit at the injection site.

The following may be mentioned as examples of AP that can be associated with the polyamino acids according to the invention, whether or not they are in the form of nanoparticles or microparticles:

proteins such as insulin, interferons, growth hormones, interleukins, erythropoietin or cytokines;

peptides such as leuprolide or cyclosporin;

small molecules such as those belonging to the anthracycline, taxoid or camptothecin family;

and mixtures thereof.

The invention will be understood more clearly and its advantages and variants will become clearly apparent from the Examples below, which describe the synthesis of the polyamino acids grafted with a hydrophobic group, their conversion to an AP vectorization system (stable aqueous colloidal suspension) and the demonstration of the ability of such a system to associate with AP (small organic molecules, proteins, etc.) to form pharmaceutical compositions.

EXAMPLE 1

Preparation of Polymer P1

Synthesis of a Polyglutamate Grafted with Palmitic Acid via a Lysine "Spacer"

1/Synthesis of the Hydrophobic Graft ($LysC_{16}$)

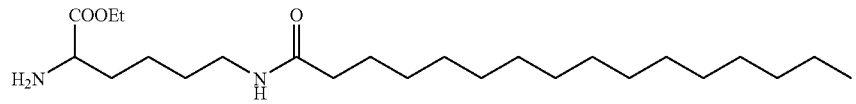

11.9 g of thionyl chloride are added in the cold to L-lysine hydrochloride (11 g) in 100 ml of ethanol and the mixture is refluxed for 3 h. After evaporation of the excess thionyl chloride and ethanol, the product is washed with heptane and then dried under vacuum to give 14.8 g of lysine bishydrochloride in which the acid group is esterified with ethanol. This product (4.9 g) is reacted with 7 g of the N-hydroxysuccinimide derivative of palmitic acid (Rn Cas 14464-31-4, available from Sigma) in an acetone/water mixture (80+40 ml respectively), in the presence of 7 g of triethylamine. After one night at room temperature, the product is precipitated by adding 1 N hydrochloric acid. After purification by passage over a silica column, 3.3 g of the desired product are recovered. Its structure is confirmed by NMR spectroscopy.

2/Synthesis of the Polymer 4 g of an alpha-L-polyglutamate (having a molecular weight equivalent to about 10,000, relative to a polyoxyethylene standard, and obtained by the polymerization of monomers consisting of N-carboxy anhydride derivatives of methyl glutamate: NCAGluOMe, followed by hydrolysis, as described in patent application FR 2 801 226) are solubilized in 80 ml of dimethylformamide (DMF) by heating at 40° C. for 2 hours. Once the polymer is solubilized, the temperature is allowed to drop to 25° C. and 1.025 g of the hydrophobic graft LysC16, previously solubilized in 6 ml of DMF, 0.06 g of 4-dimethylaminopyridine, previously solubilized in 6 ml of DMF, and 0.37 g of diisopropylcarbodiimide, previously solubilized in 6 ml of DMF, are added in succession. After 8 hours at 25° C., with stirring, the reaction medium is poured into 800 ml of water containing 15% of sodium chloride and hydrochloric acid (pH 2). The precipitated polymer is then recovered by filtration and washed with 0.1 N hydrochloric acid and then with water. The polymer is subsequently solubilized in 75 ml of DMF and then precipitated in water containing, as previously, salt and acid to pH 2. After two washes with water, the precipitate is washed several times with diisopropyl ether. The polymer is then dried in an oven under vacuum at 40° C. to give a yield in the order of 95%.

The grafting rate estimated by proton NMR is about 8.1%.

EXAMPLE 2

Preparation of Polymer P2

Polymer P2 is prepared under the same conditions as those used for polymer P1 except that the grafting rate is reduced.

The characteristics of the two polymers are collated in the Table below.

TABLE 1

| Polymer | Graft | Grafting rate (NMR) | Mn* g/mol (equiv. PMMA) |
|---|---|---|---|
| P1 | $LysC_{16}$ | 8.1% | 17,800 |
| P2 | $LysC_{16}$ | 4.9% | 15,900 |

*Mn: number-average molecular weight

In all cases, the amount of lysine-$C_{16}$ actually grafted was confirmed by NMR.

EXAMPLE 3

Analysis of the Polymers in Aqueous Solution

The polymers are dissolved in a saline phosphate buffer of pH 7.4 at a concentration of 10 to 40 mg/ml and the pH is adjusted to 7.4 by adding 0.1 N sodium hydroxide solution. The solubilization is observed visually.

TABLE 2

Solubility in aqueous saline solution at pH 7.4

| Polymer | Grafting rate | Concentration | Appearance |
|---|---|---|---|
| P1 | 8.1% | 10 mg/ml | soluble and clear |
| P2 | 4.9% | 10 mg/ml | soluble and clear |

Phosphate buffer: 0.01 M phosphate, 0.0027 M KCl and 0.137 M NaCl

Analysis of the solutions at about 1 mg/ml by light scattering (488 nm) reveals the presence of nanometric objects in the order of 100 nm for polymer P1 and the absence of objects for polymer P2 (absence of light scattering).

EXAMPLE 4

Aqueous Stability of Polymer P1

For this study, polymer P1 was compared with an analogous polymer having a hexadecanol chain grafted onto a polyglutamate via an ester group (polymer C1; grafting rate of 9.5 mol %). The synthesis of this type of analogous polymer is described in patent WO-A-00/30618.

"Accelerated" conditions were used in this study: the two polymers were left to stand at a concentration of 30 g/l, at a pH of 10 and at 60° C. for 5 days. The polymers are then analyzed by NMR after prior precipitation with 1 N HCl and washes with diisopropyl ether. The results are given in Table 3 below.

TABLE 3

| Polymer | Grafting rate, t = 0 | Grafting rate, t = 5 d |
|---|---|---|
| P1 | 8.1% | 8.1% |
| C1* | 9.5% | 4.3% |

*WO-A-00/30618

These results clearly show that polymer P1 preserves the integrity of its Lys-$C_{16}$ hydrophobic groups under high pH and temperature conditions. On the other hand, its $C_{16}$ analog suffers a loss of more than 50% of these hydrophobic alkyl groups.

EXAMPLE 5

Adsorption of a Dye Onto Polymers P1 and P2

According to one of the objects of the invention, the polymers can be used in water and associate or encapsulate an active principle (in the form of a colloidal or non-colloidal suspension). For this application, it is demonstrated in the following experiment that polymers P1 and P2 are capable of associating or encapsulating a standard dye.

The study is carried out in the following manner: the polymers are solubilized in an aqueous solution of pH 7 (phosphate buffer) and 5 mg of the dye called. "Orange OT" (Rn CAS: 2646-17-5) are added. The solutions are left in an ultrasonic bath for one hour to effect the association. The solutions are then centrifuged to remove the non-associated dye and the optical density (OD) is measured at the γmax of the dye (495 nm) after dilution.

TABLE 4

| Polymer | Grafting rate | Polymer concentration | Induced OD |
| --- | --- | --- | --- |
| P1 | 8.1 mol % | 13 mg/ml | 0.15 |
| P2 | 4.9 mol % | 20 mg/ml | 0.25 |
| Polyglutamate | 0 mol % | 25 mg/ml | 0.016 |

EXAMPLE 6

Association of the Polymers with Insulin

An aqueous solution of pH 7.4 containing 10 mg of polymer per milliliter and 200 IU of insulin (7.4 mg) is prepared. The solutions are incubated for two hours at room temperature and the free insulin is separated from the associated insulin by ultrafiltration (threshold at 100 kDa, 15 minutes under 10,000 G at 18° C.). The free insulin recovered from the filtrate is then quantitatively determined by HPLC (high performance liquid chromatography) and the amount of associated insulin is deduced.

The results show that the two polymers P1 and P2 are capable of associating insulin at a rate greater than 190 IU (7.2 mg) per 10 mg of polymer.

We claim:

1. A polyamino acid comprising aspartic units, glutamic units, or both aspartic and glutamic units; wherein at least one aspartic unit or at least one glutamic unit is bonded to a graft by a spacer comprising at least two amide linkages; wherein each graft comprises at least one hydrophobic unit; and wherein the polyamino acid is characterized by general formula (I) below:

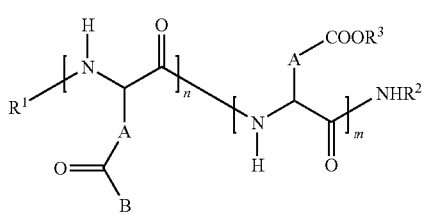

(I)

in which
   $R^1$ is H, a linear C2 to C10 acyl group or branched C3 to C10 acyl group, or a pyroglutamate;
   $R^2$ is H, a linear C2 to C10 alkyl or branched C3 to C10 alkyl, benzyl or a terminal amino acid unit;
   $R^3$ is H, a metal, an organic cation, or a cationic polyamino acid;
   the n groups B independently of one another are each a monovalent radical of the following formula:

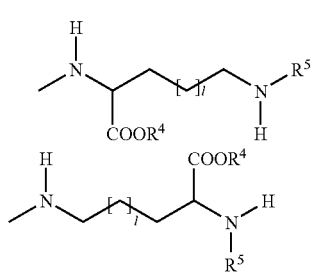

(B)

wherein:
   $R^4$ independently is a group selected from the list given for $R^3$, a linear C1 to C6 alkyl, a branched C3 to C8 alkyl, or a benzyl;
   and $R^5$ independently is a group selected from acid derivatives derived from (i) saturated or unsaturated, linear C2 to C24 alkyls or branched C4 to C24 alkyls, or (ii) C7 to C24 aryls, aralkyls or alkylaryls;
   A independently is —$CH_2$— (aspartic unit) or —$CH_2$—$CH_2$— (glutamic unit);
   n/(n+m) is defined as the molar grafting rate and varies from 0.5 to 100 mol %;
   n+m varies from 3 to 1000
   and l is equal to 1 or 2.

2. The polyamino acid according to claim 1, comprising at least one $R^5$ that is an acyl of a natural fatty acid selected from the group consisting of palmitic acid, stearic acid, oleic acid and linoleic acid.

3. The polyamino acid according to claim 1, wherein l is equal to 2 (lysine spacer).

4. The polyamino acid according to claim 1, wherein A is —$CH_2$—$CH_2$— (glutamic unit).

5. The polyamino acid according to claim 1, wherein A is —$CH_2$— (aspartic unit).

6. The polyamino acid according to claim 1, wherein A is alternately —$CH_2$—$CH_2$— (glutamic unit) or —$CH_2$— (aspartic unit).

7. The polyamino acid according to claim 1, wherein the distribution of aspartic units bonded to hydrophobic grafts, glutamic units bonded to hydrophobic grafts, or both aspartic bonded to hydrophobic grafts and glutamic units bonded to hydrophobic grafts is such that the polyamino acid is random, of the block type, or of the multiblock type.

8. The polyamino acid according to claim 1, wherein the molecular weight of the polyamino acid is between 2000 and 100,000 g/mol.

9. The polyamino acid according to claim 1, wherein the molar grafting rate n/(n+m) is between 2 and 50 mol %.

10. A pharmaceutical, cosmetic, dietetic or phytosanitary composition comprising at least one polyamino acid according to claim 1.

11. The composition according to claim 10, wherein the composition comprises at least one active principle.

12. The composition according to claim 11, wherein the active principle is a protein, a glycoprotein, a protein bonded to one or more polyalkylene glycol chains, a polysaccharide, a liposaccharide, an oligonucleotide, a polynucleotide or a peptide.

13. The composition according to claim 11, wherein the active principle is a small hydrophobic, hydrophilic or amphiphilic organic molecule.

14. The composition according to claim 10, wherein the composition can be administered by the oral, parenteral, nasal, vaginal, ocular, subcutaneous, intravenous, intramuscular, intradermal, intraperitoneal, intracerebral or buccal route.

15. The composition according to claim 10, wherein the composition is in the form of a gel, an emulsion, micelles, nanoparticles, microparticles, a powder or a film.

16. The composition according to claim 10, wherein the composition is a colloidal suspension of nanoparticles and/or microparticles and/or micelles of polyamino acids in an aqueous phase.

17. The composition according to claim 10, wherein the composition is in the form of a solution in a biocompatible solvent and that can be injected by the subcutaneous or intramuscular route or into a tumor.

18. The composition according to claim 10, wherein the composition forms a deposit at the injection site.

19. The polyamino acid according to claim 1, wherein n+m varies from 30 to 300.

20. The polyamino acid according to claim 1, wherein $R^3$ is a metal cation selected from the group consisting of sodium, potassium, calcium, and magnesium.

21. The polyamino acid according to claim 1, wherein $R^3$ is an organic cation, selected from the group consisting of cations based on amine, cations based on oligoamine, cations based on polyamine, cations based on polyethylenimine, and cations based on amino acid(s).

22. The polyamino acid according to claim 1, wherein $R^3$ is a cationic polyamino acid, selected from the group consisting of polylysine and oligolysine.

23. The polyamino acid according to claim 1, wherein the molecular weight of the polyamino acid is between 5000 and 40,000 g/mol.

24. The polyamino acid according to claim 1, wherein the molar grafting rate n/(n+m) is between 5 and 20 mol %.

25. The composition according to claim 12, wherein the active principle is a protein PEGylated with polyethylene glycol (PEG) chains.

* * * * *